United States Patent [19]

Roberts

[11] Patent Number: 4,837,192

[45] Date of Patent: Jun. 6, 1989

[54] CATALYST COMPOSITION

[75] Inventor: John S. Roberts, Bartlesville, Okla.

[73] Assignee: Phillips Petroleum Company, Bartlesville, Okla.

[21] Appl. No.: 908,558

[22] Filed: Sep. 18, 1986

Related U.S. Application Data

[60] Continuation-in-part of Ser. No. 742,818, Jun. 10, 1985, abandoned, which is a division of Ser. No. 542,960, Oct. 18, 1983, Pat. No. 4,537,994.

[51] Int. Cl.$^4$ .................. B01J 21/02; B01J 27/047; B01J 27/188
[52] U.S. Cl. .................................... 502/211; 502/210
[58] Field of Search ............... 502/208, 210, 211, 321, 502/322

[56] References Cited

U.S. PATENT DOCUMENTS

| | | | |
|---|---|---|---|
| 2,345,600 | 8/1942 | Heard et al. | 502/322 X |
| 2,440,236 | 5/1944 | Stirton | 502/208 X |
| 2,441,297 | 5/1944 | Stirton | 502/208 X |
| 2,514,282 | 7/1950 | Holden | 502/322 X |
| 2,726,195 | 12/1955 | Fleck et al. | 502/211 X |
| 2,794,005 | 5/1957 | Lefrancois | 502/322 |
| 3,076,848 | 2/1963 | Laufer | 260/609 |
| 3,715,321 | 2/1973 | Horvath | 502/210 X |
| 3,867,312 | 2/1975 | Stephens | 423/213.2 |
| 4,019,978 | 4/1977 | Miller et al. | 502/322 X |
| 4,059,636 | 11/1977 | Kubicek | 260/609 |
| 4,066,572 | 1/1978 | Choca | 502/208 X |
| 4,080,311 | 3/1978 | Kehl | 502/208 |
| 4,124,646 | 11/1978 | Kawamura | 260/609 |
| 4,146,574 | 3/1979 | Onoda et al. | 502/209 X |
| 4,219,444 | 8/1980 | Hill et al. | 502/210 |
| 4,257,922 | 3/1981 | Kim et al. | 502/321 X |
| 4,289,652 | 9/1981 | Hunter et al. | 502/210 |
| 4,289,663 | 9/1981 | Hill et al. | 502/210 X |
| 4,297,242 | 10/1981 | Hensley, Jr. et al. | 252/439 |
| 4,444,906 | 4/1984 | Callahan et al. | 502/211 |
| 4,444,965 | 4/1984 | McDaniel et al. | 526/105 |
| 4,522,934 | 6/1985 | Shum et al. | 502/209 |

FOREIGN PATENT DOCUMENTS

| | | | |
|---|---|---|---|
| 552641 | 2/1958 | Canada . | |
| 725697 | 7/1977 | U.S.S.R. | 502/322 |

OTHER PUBLICATIONS

In re Seaborg 140USPQ 659–665.
Chem. Abst. 77: 13038h (1972).
Chem. Abst. 75: 35294z (1971).
Chem. Abst. 68: 68709x (1968).
Chem. Abst. 80: 87873k (1974).
Chem. Abst. 81: 345p (1974).

Primary Examiner—W. J. Shine
Attorney, Agent, or Firm—French & Doescher

[57] ABSTRACT

Interchange reactions between organosulfides and mercaptans are promoted by the use of catalysts containing Group VIB oxides. The preferred catalysts are supported phospho Group VIB oxide acids, such as phosphotungstic acid and phosphomolybdic acid. The preferred supports are moderately acidic supports that contain aluminum, such as zinc aluminate and aluminum phosphate.

8 Claims, No Drawings

CATALYST COMPOSITION

This is a continuation in part of copending U.S. application Ser. No. 742,818 filed June 10, 1985 (now abandoned) which is a divisional of Ser. No. 542,960, filed Oct. 18, 1983 now U.S. Pat. No. 4,537,994, patented Aug. 27, 1985.

BACKGROUND

Organosulfides are useful in a number of ways. Many organosulfides are solvents, plasticizers and processing aids for various other organic materials. Some diorganosulfides, such as phenylpropylsulfide, are useful as corrosion inhibitors, hair growth stimulators, and as extractants for noble metals.

The preparation of organosulfides using mercaptans as reactants involves a metathesis, or interchange, reaction between the organic radical of the mercaptan and one or more of the organic substituents of an organosulfide reactant. Such reactions generally have low conversion and selectivity values.

INVENTION

It has been discovered that the reaction of certain organosulfides with mercaptans to yield substitution, or metathesis, products, can be more effectively carried out in the presence of Group VIB oxides, such as supported phosphotungstic or phosphomolybdic acid catalysts.

In one embodiment, alkyl aryl sulfides are prepared from thiophenol by reacting it with dialkyl sulfides over an alumino phosphotungstic acid catalyst. For example, when a mixture of a di-n-propyl sulfide and thiophenol is passed over a hot (580° F.) catalyst prepared from aluminum phosphate and phosphotungstic acid, a 12% sulfide conversion results in a product having a 90.5% selectivity to phenyl n-propylsulfide.

OBJECTS OF THE INVENTION

It is one object of the present invention to provide catalysts useful for assisting in the reaction of organic sulfides with mercaptans to yield metathesis or interchange products.

It is another object of the present invention to provide a process for producing these catalysts.

It is yet another object of the present invention to provide a process by which such interchange reactions can be carried out.

ADVANTAGES

The catalysts and processes of the invention have several advantages over the prior art. Specifically, reactions carried out in accordance with the invention have good conversion rates and high selectivities to desired products.

Other advantages and aspects of the invention will become apparent from a consideration of the following description.

DESCRIPTION OF THE INVENTION

Reactants

The reactants with which the invention are concerned take part in interchange reactions involving mercaptans, i.e., thiols or thioalcohols, and sulfides, i.e., thioethers. Generally, these reactions involve interactions in which at least one organic moiety of a diorganosulfide is replaced by an organic moiety from a mercaptan.

The general reaction scheme can be represented by:

$$R-S-R + R'SH \rightarrow R-S-R' + RSH.$$

In the above formulas, R and R' are independently selected from the group consisting of alkyl, cycloalkyl, aromatic, alklaryl, arylalkyl, straight chain or branched chain groups, with the R's being the same or different in the same molecule. Generally, the R and R' groups are selected so that sulfides and mercaptans to be used contain from about 2 to about 40 carbon atoms per molecule, preferably from about 2 to about 16.

Sulfides useful in the invention are exemplified by the sulfides disclosed in U.S. Pat. No. 4,059,636, the disclosure of which is hereby incorporated by reference.

The organic sulfides employed in the practice of this invention include those of general formula R—S—R; wherein the R groups are as defined above.

Examples of useful sulfides include dimethyl sulfide, diethyl sulfide, diisopropyl sulfide, di-n-butyl sulfide, di-n-octyl sulfide, di-n-dodecyl sulfide, di-n-eicosyl sulfide, methyl ethyl sulfide, n-pentyl-n-heptyl sulfide, dicyclohexyl sulfide, bus(4-methylcyclo-hexyl)sulfide, diphenyl sulfide, di-p-tolyl sulfide, bis(p-n-hexylphenyl)sulfide, dibenzyl sulfide, and the like. Mixtures of sulfides as well as mixtures of sulfide with other inert components are feedstocks within the scope of this invention.

Useful mercaptans correspond to the sulfides discussed above. That is, they are the formula R'SH in which R' is independently selected from the groups of moieties defined above.

Examples of useful mercaptans include alkylthiols, e.g., methyl mercaptan (methanethiol), ethyl mercaptan (ethanethiol), octyl mercaptan (octanethiol) and the like; aromatic thiol, e.g., phenyl mercaptan (thiophenol), napthyl mercaptans (napthylene thiols), and the like. Phenyl mercaptan and alkylphenyl mercaptans are preferred. Substituted forms of these mercaptans, i.e., compound containing branched chain and/or non-functional substituents are operable. Mixtures of mercaptan reactants are operable.

While the use of stoichiometric quantities of reactants can be inferred from the above equation, quantities other than stoichiometric amounts are operable. Generally sulfide:mercaptan mole ratios of about 1:1 to about 1:10 with about 1:1.01 to about 1:5 preferred, can be used. While the presence of an excess of either reactant can be tolerated, it is preferred that, when excess reactant is used, it be the mercaptan (thiol) which is present in excess. This is primarily because of the relative ease of separation due to high volatility of the mercaptan and in part because of economics.

The use of more than one sulfide and more than one mercaptan in combination is contemplated.

Catalysts

The catalysts of the present invention can be used with or without the support; however, it is preferred that the catalyst be a supported catalyst.

The supported catalysts useful herein are derivatives of Group VIB oxide components, preferably molybdenum oxide and tungsten oxide components, and are produced by contacting these components with suitable supports.

Suitable tungsten oxide and molybdenum oxide components include phosphotungstic and phosphomolybdic acid, their hydrates, metal salts, and the like. Mixtures of molybdenum and tungsten oxide components can be employed.

Preferred catalysts are phospho Group VIB oxide acids. Catalysts more preferred are supported phospho Group VIB oxide acids. The catalyst most preferred are supported phosphotungstic or phosphomolybdic acid catalysts.

When supported, useful support components include activated carbon, alumina, aluminum phosphate, zinc aluminate, silica alumina, zirconia, silica, thoria, pumice, and the like and mixtures of any two or more thereof. The more preferred support is one that has the characteristic of being moderately acidic. The moderately acidic catalyst supports that are most preferred contain aluminum, and are preferably zinc aluminate and aluminium phosphate. It is also preferred that the final supported catalyst of the present invention be moderately acidic.

One preferred catalyst is an aluminophosphotungstic acid catalyst prepared by reacting an aluminum-containing compound with phosphotungstic acid; such a catalyst is phosphotungstic acid on aluminum phosphate.

Another preferred catalyst is an aluminophosphomolybdic acid catalyst prepared by reacting an aluminum-containing compound with phosphomolybdic acid; such a catalyst is phosphomolybdic acid on zinc aluminate.

The amount of catalytically active Group VIB oxide component that is reacted and impregnated onto the support generally ranges from about 0.01 weight percent to about 10 weight percent based on the total weight of the catalyst. A preferred concentration range of the catalytically active Group VIB oxide component on the support is within the range of about 0.5 to about 3 weight percent based on the total weight of the catalyst. A most preferred range of catalytically active Group VIB oxide component on support is within the concentration range of about 1 to about 2 weight percent based on the total weight of the catalyst.

It is important that the catalyst of the present invention be sulfided. It is preferred that the present catalyst be presulfided prior to contacting the reactants in the reaction mixture since a non-sulfided catalyst will waste the reactants by using up the sulfur from the reactants until the catalyst is fully sulfided.

Compounds for presulfiding can be any sulfur containing compound where the sulfur is readily available, such as hydrogen sulfide, mercaptans, sulfides, disulfides, polysulfides, and the like and mixtures of any two or more thereof. The pressure, flow rate, and time for sulfiding the catalyst with the sulfur containing compound is not critical so long as it is conducted under conditions sufficient to effectively sulfide the catalyst. Generally, the temperature range will be between about 150° C. to about 400° C. preferably about 200° C. to about 300° C., most preferably about 260° C.

The amount of sulfur, from the sulfur containing compound, that is needed to flow over the catalyst is at least about 1 mole per mole of Group VIB metal oxide present in the catalyst. The amount of sulfur that flows over the catalyst is preferably within the range of about 1 to about 10 moles per mole of Group VIB metal oxide present in the catalyst.

The phospho Group VIB acids that are used to prepare the preferred catalysts are readily available, but can be prepared by reacting the Group VIB oxide with phosphoric acid.

The amount of catalyst employed in the instant reactions generally ranges from about 0.01 weight percent to about 1 weight percent based on the weight of the total reaction mixture.

The catalyst can be regenerated when necessary by heating in oxygen and then passing a sulfur compound, such as $H_2S$, over the catalyst at elevated temperature.

A supported catalyst of the present invention is made by (a) adding the support material to a solution of Group VIB oxide component in polar diluent;

(b) mixing the material from step (a) for a sufficient length of time to allow the Group VIB oxide component to react and impregnate onto the support, thereby forming a supported catalyst;

(c) drying the supported catalyst of step (b) thereby forming a dried catalyst; and (d) presulfiding the dried catalyst of step (c) under conditions sufficient to effectively sulfide the catalyst.

The amount of polar diluent used in the solution can vary greatly depending upon the solubility of the Group VIB oxide, the size of the container, and the preferred drying time. It is preferred however, that the ratio of Group VIB oxide component to polar diluent be within the range of about 5 grams to about 0.05 grams Group VIB oxide per hundred milliliters of diluent.

The drying in step (c) is preferably done under vacuum at elevated temperature.

The preferred polar diluent in the solution of step (a) is water.

REACTION CONDITIONS

The metathesis reactions carried out in accordance herewith involve well-known reaction parameters. The following are merely suggestions from which the skilled artisan can extrapolate.

Useful reaction conditions for the inventive process include those under which conversions of the instant type occur, i.e, those under which, for example, dialkyl sulfides react with aromatic mercaptans to produce alkyl aryl sulfides.

If desired, an inert diluent can be employed in the feedstream to dilute or fluidize the feedstream. Such diluents may be especially desirable with higher molecular weight organic sulfides to facilitate flow to and from the reactor. Such diluents include hydrocarbons such as pentane, hexane, benzene, toluene, xylenes, etc. They can be used in any suitable amounts.

The above-described ingredients of the feedstream are intimately mixed by any suitable means and are then contacted with the catalyst in any suitable reaction zone under sulfide-cleaving conditions to produce the desired results. This invention is especially well suited for the use of a continuous reactor, but, if desired, a batch reactor can be employed.

Reaction temperatures can vary widely depending on other reaction conditions. Temperature can also depend on the reactivity of the sulfide feedstock and on the degree of sulfide cleavage desired. Generally, temperatures in the range of about 350° to about 700° F. (177° to 371° C.) are employed using presently available commercial catalysts. The use of the phosphotungstic acid catalyst permits good conversion and selectivity in a temperature range of about 350° to about 600° F. (177° to 315° C.) It is preferable, because of the principal reaction rate, side-reactions, etc., to employ temperatures in the range of about 350° to about 550° F. (232° to about 288° C.).

Reaction pressures can vary widely. Usually, pressures in the range of about 100 to about 5000 psig can be used, although, as a matter of convenience, pressures of about 100 to about 750 psig are normally preferred.

Contact time of the reactants with catalyst under suitable sulfide-cleaving conditions can vary widely depending on desired degree of sulfide-cleavage and other reaction conditions. However, weight hourly space velocities (weight feed/weight catalyst/hour) in the range of about 0.1 to about 10, and preferably about 0.2 to about 1, are normally employed.

The following examples illustrate the invention.

EXAMPLE I

This example describes the preparation of the catalysts employed in this invention. A mixture of 100 grams of zinc aluminate, 1.27 grams phosphomolybdic acid and 200 milliliters of water was stirred at ambient room temperature for two hours after which the water was removed under vacuum at 90°–100° C. The wet catalyst was further dried and activated according to the procedure described in Example II.

Another catalyst system was similarly prepared from 27 grams of aluminum phosphate (containing 1 percent chromic and boric acid), 0.5 grams of phosphotungstic acid and 15 milliliters of methyl alcohol.

EXAMPLE II

This example describes two inventive runs employing the catalysts as prepared in Example I. A stainless steel tubular reactor with heaters (0.5 inch diameter × 18 inch length) was charged with 10 milliliters of glass beads, 50 grams (70 milliliters) of wet catalyst from Example I, and another 10 milliliters of glassbeads. The system was purged with nitrogen at 316° C. (600° F.) to dry the catalyst and activated by passing $H_2S$ over the catalyst for 4 hours at 316° C./100 psig. The reactor contents were then maintained at a set temperature and pressure while a mixture of thiophenol and di-n-propyl sulfide at a mole ratio of about 1.04:1 was metered through the reactor using a LS-30 Lapp pump. On the downstream side, pressure was controlled and products removed by a Whitey 2 RF 2 valve operated by a Taylor Fulscope. A valved needle assembly was placed in the line after pressure let-down to provide intermittent sampling of liquid into cooled, capped Diels-Alder tubes. Samples were analyzed by GLC using a 12 foot × 0.125 inch column packed with 10° SE 30 on acid-washed dimethylchlorosilane treated chromosorb programmed at 30 degrees per minute between 50° C. and 300° C. The results are listed in Table I for the two catalysts studied. These results show both catalyst systems effective in producing n-propyl phenyl sulfide from di-n-propyl sulfide and thiophenol, the phosphomolybdic acid catalyst giving a higher di-n-propyl sulfide conversion and a higher n-propyl phenyl sulfide selectivity than the phosphotungstic acid catalyst. Most of the difference between the two catalysts in Table I is due to the lower weight hourly space velocity (WHSV) used with the phosphomolybdic acid catalyst.

TABLE I

Preparation of n-Propyl Phenyl Sulfide From
Di-n-Propyl Sulfide and Thiophenol
Press. 350 psig Catalyst 1
Press. 450 psig Catalyst 2
Mole Ratio Thiophenol/sulfide = 1

| Catalyst | Mid Bed Temp(°C.) | Feed Preheat | WHSV hr.$^{-1}$ | Conv. | Selec. |
|---|---|---|---|---|---|
| 1. 1.8% Phosphotungstic Acid on Aluminum Phosphate | 304.4 | 251.7 | 6.27 | 12.3 | 90.5 |
| 2. 1.17% Phosphomolybdic Acid on Zinc Aluminate | 299.4 | 281.7 | 0.79 | 51.4 | 94.1 |

The following runs were conducted to show the activity of a catalyst of the present invention in which the concentration of catalytically active Group VIB oxide on support is at the extremities of the preferred range of about 0.01 to about 10 weight percent.

EXAMPLE III

Catalysts with varying concentrations of phosphomolybdic acid were made by adding to a 350 ml round bottom flask, 100 g of zinc aluminate and phosphomolybdic acid (11 g or 0.1 g, respectively) in 200 ml of water. The mixture was rolled on a rotovap for 1 hour and then dried on the rotovap using a water aspirator vaccum and steam heat. The catalyst was loaded into a stainless steel tubular reactor. It was then heated to 260° C. under a dynamic stream of hydrogen sulfide maintained at 100 psig. After 4 hours, the catalyst was cooled to room temperature under nitrogen.

EXAMPLE IV

A mixture of thiophenol and di-n-propyl sulfide (mole ratio = 1) was metered past the catalyst using a Lapp LS-30 pump. On the downstream side, the pressure was controlled at 110 psig using a Moore Flow Controller. The entire product was captured in a Buchner funnel with attachment to a flare line. The weight of feed and product were obtained at the end of 6–8 hours run. The product was analyzed at this point. The product was analyzed using a 12' × 0.124" column packed with 10% Dexil 300 on Chromosorb (AW-DMCS). The chromatograph was temperature programmed from 50° C. to 300° C. at 15° C./minute.

The following data was obtained for the catalysts with varying phosphomolybdic acid:

TABLE II

Preparation of n-Propyl Phenyl Sulfide from
Di-n-Propyl Sulfide and Thiophenol Using
Phosphomolybdic Acid on Zinc Aluminate
Press. 110 psig
Mole Ratio Thiophenol/Sulfide = 1

| % Phosphomolybdic Acid on Zinc Aluminate | Mid Bed Temp (°C.) | Feed Preheat (°C.) | WHSV hr.$^{-1}$ | Conv. | Selec. |
|---|---|---|---|---|---|
| 9.91% | 292.6 | 191.3 | 0.34 | 30.6 | 47.0 |

TABLE II-continued

Preparation of n-Propyl Phenyl Sulfide from
Di-n-Propyl Sulfide and Thiophenol Using
Phosphomolybdic Acid on Zinc Aluminate
Press. 110 psig
Mole Ratio Thiophenol/Sulfide = 1

| % Phosphomolybdic Acid on Zinc Aluminate | Mid Bed Temp (°C.) | Feed Preheat (°C.) | WHSV hr.$^{-1}$ | Conv. | Selec. |
| --- | --- | --- | --- | --- | --- |
| 9.91% | 292.3 | 191.6 | 0.25 | 31.9 | 45.3 |
| 0.1% | 293.7 | 198.5 | 0.26 | 41.9 | 80.0 |
| 0.1% | 291.2 | 204.2 | 0.29 | 40.1 | 85.0 |

The percent conversion of a particular catalyst depends upon its activity and the weight hourly space velocity (WHSV hr.$^{-1}$). As shown above in Table II, the WHSV of the feed is quite a bit lower than the WHSV of the feed in Table I. A WHSV of about 2 hr.$^{-1}$ was tried with the catalysts in Table II; however, the rate was so fast that the conversion was very poor indicating that the Table II catalysts are not as active as the Table I catalysts (the catalysts of Table I are in the preferred range). Even at the lower WHSV of Table II the conversion and selectivity of the catalysts in Table II are not as good as the conversion and selectivity of the catalysts in Table I. Catalysts with the Group VIB oxide at lower or higher concentration than the general range of 0.01 to 10 weight percent would show poorer conversion and selectivity.

The results above show that the catalysts of the present invention are effective within the general range of about 0.01 to about 10 weight percent active material on a support. The activity of catalysts that have a concentration of active material beyond the general range would be too low to be useful for the present invention. The results above also show the catalysts that have the concentration of active material on support within the preferred and more preferred ranges of the present invention are very active.

Reasonable variations, such as those which would occur to the skilled artisan may be made herein without departing from the scope of the invention.

I claim:

1. A composition useful as a catalyst for interactions between organic sulfides and mercaptans, which composition comprises:
   a sulfided phospho Group VIB oxide acid on a moderately acidic aluminum containing support selected from the group consisting of metal aluminates,
   wherein said phospho Group VIB oxide acid on said support is within the range of about 0.01 to about 10 weight percent based on the total weight of the catalyst.

2. A composition according to claim 1 wherein said phospho Group VIB oxide acid is selected from the group consisting of phosphomolybdic acid and phosphotungstic acid.

3. A composition according to claim 2 wherein said support is zinc aluminate.

4. A composition according to claim 3 wherein said composition comprises sulfided phosphomolybdic acid on zinc aluminate.

5. A composition according to claim 1 wherein said phospho Group VIB oxide acid on said support is within the range of about 0.5 to about 3 weight percent based on the total weight of the catalyst.

6. A composition according to claim 5 wherein said phospho Group VIB oxide acid on said support is within the range of about 1 to about 2 weight percent based on the total weight of the catalyst.

7. A composition useful as a catalyst for interactions between organic sulfides and mercaptans, which composition consists essentially of:
   the reaction product of (a) a phospho Group VIB oxide acid reactant selected from (1) phosphomolybdic acid and (2) phosphotungstic acid reacted with (b) a moderately acidic aluminum containing support selected from (3) metal aluminates.

8. A composition according to claim 7 wherein said phospho Group VIB oxide acid reactant is phosphomolybdic acid and said moderately acidic aluminum containing support is zinc aluminate.

* * * * *